(12) United States Patent
Honda et al.

(10) Patent No.: US 8,405,042 B2
(45) Date of Patent: Mar. 26, 2013

(54) PARTICLE BEAM THERAPY SYSTEM

(75) Inventors: Taizo Honda, Tokyo (JP); Hisashi Harada, Tokyo (JP); Yuehu Pu, Tokyo (JP); Yuichi Yamamoto, Tokyo (JP); Takaaki Iwata, Tokyo (JP)

(73) Assignee: Mitsubishi Electric Corporation, Chiyoda-Ku, Tokyo (JP)

( * ) Notice: Subject to any disclaimer, the term of this patent is extended or adjusted under 35 U.S.C. 154(b) by 279 days.

(21) Appl. No.: 12/864,002

(22) PCT Filed: Jan. 28, 2010

(86) PCT No.: PCT/JP2010/051121
§ 371 (c)(1),
(2), (4) Date: Jul. 22, 2010

(87) PCT Pub. No.: WO2011/092815
PCT Pub. Date: Aug. 4, 2011

(65) Prior Publication Data
US 2011/0260074 A1    Oct. 27, 2011

(51) Int. Cl.
*G21K 1/08* (2006.01)
(52) U.S. Cl. .......... 250/396 R; 250/505.1; 250/396 ML; 250/492.1; 250/492.3; 250/493.1; 313/359.1; 315/502; 315/503; 315/505; 378/157; 378/152; 378/62
(58) Field of Classification Search .............. 250/505.1, 250/396 R, 396 ML, 492.1, 492.3, 493.1; 313/359.1; 315/502, 503, 505; 378/147, 378/152, 65
See application file for complete search history.

(56) References Cited

U.S. PATENT DOCUMENTS

| | | | | |
|---|---|---|---|---|
| 6,677,597 B1 * | 1/2004 | Haberer et al. | ............ | 250/491.1 |
| 6,799,068 B1 * | 9/2004 | Hartmann et al. | ................ | 607/2 |
| 7,636,419 B1 * | 12/2009 | Nelson | ............................ | 378/65 |
| 2005/0247890 A1 * | 11/2005 | Norimine et al. | .......... | 250/492.3 |
| 2006/0033042 A1 * | 2/2006 | Groezinger et al. | ....... | 250/492.1 |

(Continued)

FOREIGN PATENT DOCUMENTS

| | | |
|---|---|---|
| JP | 2001-257100 A | 9/2001 |
| JP | 2005-296162 A | 10/2005 |

(Continued)

OTHER PUBLICATIONS

*International Search Report for PCT/JP2010/051121, completed Feb. 10, 2010 (in Japanese).

*Primary Examiner* — Michael Logie
(74) *Attorney, Agent, or Firm* — Buchanan Ingersoll & Rooney PC

(57) ABSTRACT

The objective of the present invention is to reduce the effect of the hysteresis of a scanning electromagnet so as to obtain a particle beam therapy system that realizes high-accuracy beam irradiation. There are included an irradiation management apparatus (32) that controls the scanning electromagnet (3), based on target irradiation position coordinates (Pi) of a charged particle beam (1b), and a position monitor (7) that measures measurement position coordinates (Ps) of the charged particle beam (1b). The irradiation management apparatus (32) has a command value creator (25) that outputs a control input (Io (Ir)) to the scanning electromagnet (3), based on the target irradiation position coordinates (Pi) and correction data (Ia) created on the basis of the measurement position coordinates (Ps), measured by the position monitor (7) in the preliminary irradiation in which the excitation pattern of the scanning electromagnet is the same as that of the main irradiation plan, and the target irradiation position coordinates (Pi).

9 Claims, 7 Drawing Sheets

U.S. PATENT DOCUMENTS

| | | | |
|---|---|---|---|
| 2007/0051905 A1* | 3/2007 | Fujimaki et al. | 250/492.3 |
| 2007/0114473 A1* | 5/2007 | Matsuda et al. | 250/505.1 |
| 2009/0039256 A1* | 2/2009 | Fujii et al. | 250/306 |
| 2009/0168960 A1* | 7/2009 | Jongen et al. | 378/65 |
| 2010/0127183 A1* | 5/2010 | Iseki et al. | 250/396 ML |
| 2010/0183121 A1* | 7/2010 | Riker et al. | 378/65 |

FOREIGN PATENT DOCUMENTS

| | | | |
|---|---|---|---|
| JP | 2005296162 A | * | 10/2005 |
| JP | 2007-132902 A | | 5/2007 |

* cited by examiner

PARTICLE BEAM THERAPY SYSTEM

TECHNICAL FIELD

The present invention relates to a particle beam therapy system utilized in the medical field and R&Ds and particularly to a particle beam therapy system of a scanning type such as a spot-scanning type or a raster-scanning type.

BACKGROUND ART

In general, a particle beam therapy system is provided with a beam generation apparatus that generates a charged particle beam; an accelerator that is connected with the beam generation apparatus and accelerates a generated charged particle beam; a beam transport system that transports a charged particle beam that is accelerated by the accelerator so as to gain predetermined energy and then emitted; and a particle beam irradiation system, disposed at the downstream side of the beam transport system, for irradiating an irradiation subject with a charged particle beam. Particle beam irradiation systems are roughly divided into a broad irradiation method in which a charged particle beam is enlarged in a scattering manner by a scatterer, and the shape of the enlarged charged particle beam is made to coincide with the shape of an irradiation subject in order to form an irradiation field; and a scanning irradiation method (the spot-scanning method, the raster-scanning method, and the like) in which an irradiation field is formed by performing scanning with a thin, pencil-like beam in such a way that the scanning area coincides with the shape of an irradiation subject.

In the broad irradiation method, an irradiation field that coincides with the shape of a diseased site is formed by use of a collimator or a bolus. The broad irradiation method is a most universally utilized and superior irradiation method where an irradiation field that coincides with the shape of a diseased site is formed so as to prevent unnecessary irradiation onto a normal tissue. However, it is required to create a bolus for each patient or to change the shape of a collimator in accordance with a diseased site.

In contrast, the scanning irradiation method is a high-flexibility irradiation method where, for example, neither collimator nor bolus is required. However, because these components for preventing irradiation onto not a diseased site but a normal tissue are not utilized, there is required a positional accuracy of beam irradiation that is the same as or higher than that of the broad irradiation method.

Patent Document 1 discloses an invention, stated below, that has an objective of providing a particle beam therapy system capable of accurately irradiating a diseased site. In the invention disclosed in Patent Document 1, there are stored, in a memory device, the amount of charged particle beams scanned by a scanning apparatus and the position of a charged particle beam detected by a beam position detector while the charged particle beam is emitted; then, by utilizing the stored scanning amount and the beam position, the scanning amount of the beam scanning apparatus is set by a control apparatus, in accordance with the beam position based on information about a treatment plan. The relationship between the scanning amount and the beam position, which is obtained by actually performing irradiation, is stored in the memory device; therefore, accurate irradiation onto a diseased site can be expected.

PRIOR ART REFERENCE

Patent Document

[Patent Document 1] Japanese Patent Application Laid-Open No. 2005-296162

DISCLOSURE OF THE INVENTION

Problem to be Solved by the Invention

In the invention disclosed in Patent Document 1, a transformation table is created based on actual data on the scanning amount and the position, of a charged particle beam, which are obtained through actual irradiation, and by utilizing this transformation table, the setting current value of a scanning electromagnet is calculated.

However, in fact, because there exist hysteresis characteristics between the current and the magnetic field of the scanning electromagnet, the magnetic field at a time when the current value increases differs from the magnetic field at a time when the current decreases. The excitation pattern, which is a pattern of increase/decrease in a current of a scanning electromagnet at a time of main irradiation where irradiation onto a diseased site is actually performed, is different from the excitation pattern of the scanning electromagnet for irradiation at a time when the transformation table is created; therefore, there has been a problem that, due to the effect of the hysteresis of the electromagnet, accurate irradiation onto the diseased site cannot be performed.

The present invention has been implemented in order to solve the foregoing problems; the objective thereof is to reduce the effect of the hysteresis of a scanning electromagnet so as to obtain a particle beam therapy system that realizes high-accuracy beam irradiation.

Means for Solving the Problem

There are included an irradiation management apparatus that controls a scanning electromagnet, based on target irradiation position coordinates of a charged particle beam; and a position monitor that measures measurement position coordinates of the charged particle beam. The irradiation management apparatus has a command value creator that outputs a control input to the scanning electromagnet, based on the target irradiation position coordinates and correction data created on the basis of the measurement position coordinates, measured by the position monitor in preliminary irradiation in which the excitation pattern of the scanning electromagnet is the same as that of a main irradiation plan, and the target irradiation position coordinates.

Advantage of the Invention

In a particle beam therapy system according to the present invention, the scanning-electromagnet excitation pattern of the preliminary irradiation is the same as that of the main irradiation, and the control input to the scanning electromagnet is corrected based on the result obtained in the preliminary irradiation; therefore, the effect of the hysteresis of a scanning electromagnet is eliminated, so that high-accuracy beam irradiation can be realized.

BEST MODE FOR CARRYING OUT THE INVENTION

Embodiment 1

Figure 1:
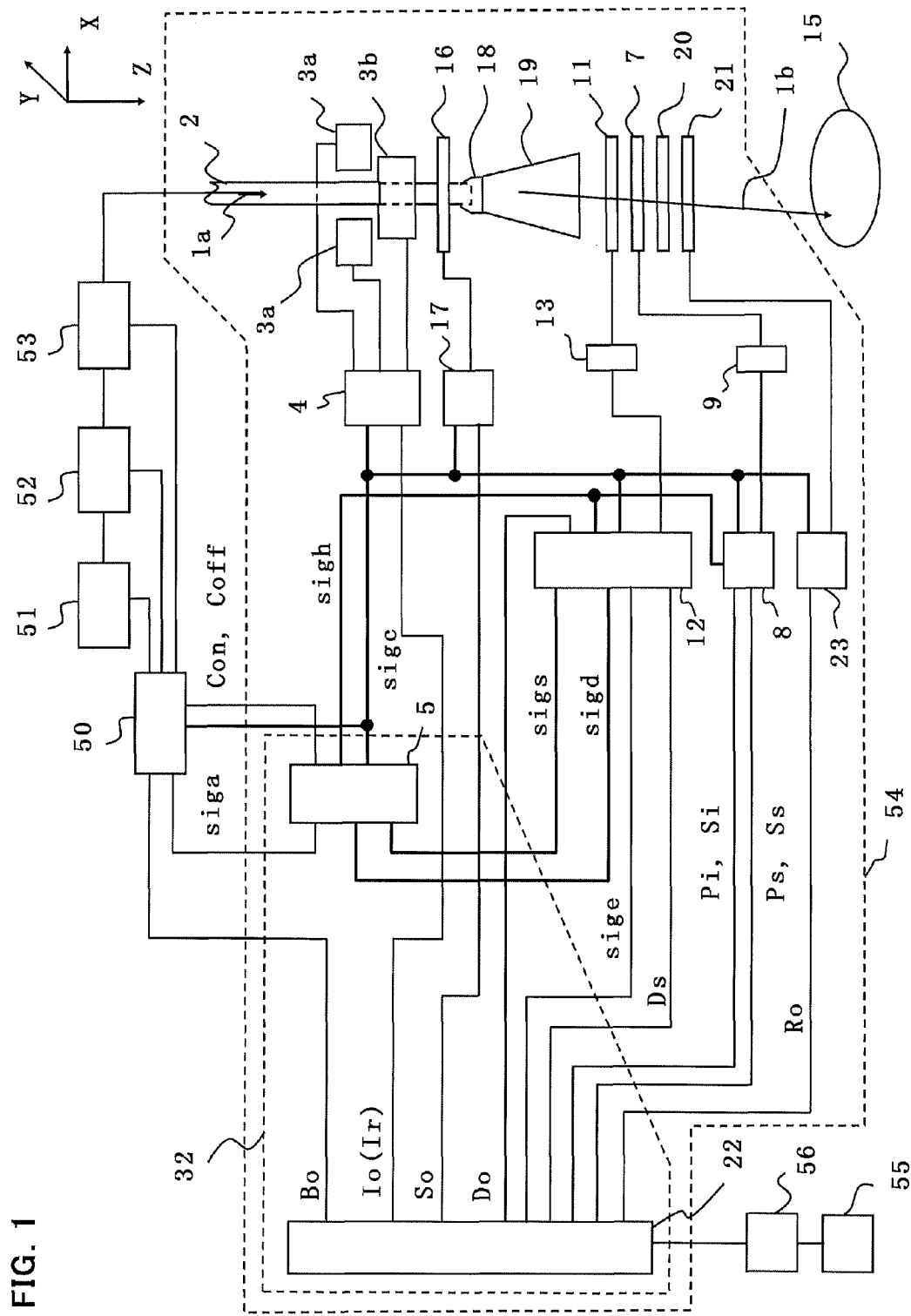
FIG. 1 is a schematic block diagram illustrating a particle beam therapy system according to Embodiment 1 of the present invention.

FIG. 1 is a schematic block diagram illustrating a particle beam therapy system according to Embodiment 1 of the present invention. The particle beam therapy system includes a beam generation apparatus 51, an accelerator 52, a beam transport apparatus 53, a beam acceleration transport control apparatus 50, a particle beam irradiation apparatus 54, a treatment planning apparatus 55, and a patient file server 56. The beam generation apparatus 51 generates a charged particle beam 1 by accelerating charged particles generated in an ion source. The accelerator 52 is connected with the beam generation apparatus 51 and accelerates a generated charged particle beam 1 up to predetermined energy. The beam transport apparatus 53 transports a charged particle beam 1 that is accelerated by the accelerator 52 so as to gain predetermined energy and then emitted. The beam acceleration transport control apparatus 50 controls the beam generation apparatus 51, the accelerator 52, and the beam transport apparatus 53. The particle beam irradiation apparatus 54 is disposed at the downstream side of the beam transport system 53 and irradiates an irradiation subject 15 with a charged particle beam 1. The treatment planning apparatus 55 determines the irradiation subject 15 of a patient based on information of an image photographed by an X-ray CT scanner or the like, and creates target irradiation position coordinates Pi0, target dose Di0, a target beam size Si0, a target accelerator setting Bi0, a range shifter insertion amount Ri0, and the like, which are treatment plan data items F0 for the irradiation subject 15. The target accelerator setting Bi0 includes the beam energy of the accelerator 52 and the setting value of a beam current. The patient file server 56 stores treatment plan data items F0 that are created by the treatment plan apparatus 55 for each patient.

The particle beam irradiation apparatus 54 is provided with a beam transport duct 2 for transporting an incident charged particle beam 1a injected by the beam transport apparatus 53; scanning electromagnets 3a and 3b that scan the incident charged particle beam 1a in the X direction and the Y direction, respectively, which are directions perpendicular to the incident charged particle beam 1a; a position monitor 7; a preamplifier 9 that amplifies a signal from the position monitor 7; a position monitor unit 8; a dose monitor 11; a preamplifier that amplifies a signal from the dose monitor 11; a dose monitor unit 12; an irradiation management apparatus 32; a scanning electromagnet power source 4; a beam enlargement apparatus 16; a beam enlargement control apparatus 17; a bellows 18; a vacuum duct 19; a ripple filter 20; a range shifter 21; and a range shifter unit 23. As illustrated in FIG. 1, the traveling direction of the incident charged particle beam 1a is the Z direction.

The scanning electromagnet 3a is an X direction scanning electromagnet that performs X-direction scanning with the incident charged particle beam 1a; the scanning electromagnet 3b is a Y direction scanning electromagnet that performs Y-direction scanning with the incident charged particle beam 1a. The position monitor 7 detects the beam size and the passing position (the position of the gravity center) of an outgoing charged particle beam 1b that has been deflected by the scanning electromagnets 3a and 3b. The preamplifier 9 amplifies analogue data on the passing position and the beam size detected by the position monitor 7. Here, the beam size denotes an area, in the XY plane perpendicular to the Z direction, through which the outgoing charged particle beam 1b passes. The position monitor unit 8 receives the passing position and the beam size detected by the position monitor 7, through the preamplifier 9; then, the position monitor unit 8 converts the passing position and the beam size into digital data so as to create measurement position coordinates Ps and a measurement beam size Ss.

The dose monitor 11 detects the dose of the outgoing charged particle beam 1b. The preamplifier 13 amplifies analogue data on the dose detected by the dose monitor 11. The dose monitor unit 12 receives the dose detected by the dose monitor 11, through the preamplifier 13; then, the dose monitor unit 12 converts the dose into digital data so as to create a measurement dose Ds.

The beam enlargement apparatus 16 enlarges the beam size of the outgoing charged particle beam 1b. The vacuum duct 19 ensures a vacuum region through which the outgoing charged particle beam 1b passes. The bellows 18 connects the beam transport duct 2 with the vacuum duct 19 in an expandable/contractible manner and extends the vacuum region toward the irradiation subject 15. The ripple filter 20 is also referred to as a ridge filter and formed in a convex shape. The ripple filter 20 causes an energy loss to the charged particle beam 1, which is a monochromatic beam having approximately single energy and transported from the accelerator 52, so that the energy has a range.

The depth-direction (Z direction) position coordinates of the irradiation subject 15 is controlled by varying the energy of the incident charged particle beam 1a through change in the acceleration energy of the accelerator 52 and by varying the energy of the outgoing charged particle beam 1b through the range shifter 21. The range shifter 21 adjusts the range of the charged particle beam 1 little by little. Considerable change of the range of the charged particle beam 1 is performed by changing the acceleration energy of the accelerator 52, and slight change of the range of the charged particle beam 1 is performed by changing the setting of the range shifter 21.

The irradiation management apparatus 32 is provided with an irradiation control apparatus 5 and an irradiation control computer 22. The irradiation control computer 22 reads the treatment plan data items F0 from the patient file server 56; then, in order to control the irradiation dose, the irradiation control computer 22 creates setting data Fi by rearranging the treatment plan data items F0 in order of irradiation onto irradiation spots, which are divided irradiation units. In other words, the setting data Fi is sequentialized treatment plan data. Based on the setting data Fi, the treatment plan data items F0 are outputted as setting data Fo, which are respective commands to the apparatuses.

The elements of the setting data Fi are target irradiation position coordinates Pi, a target dose Di, a target beam size Si, a target accelerator setting Bi, and a range shifter insertion amount Ri; respective elements of the setting data Fi are data items obtained by sequentializing the target irradiation position coordinates Pi0, the target dose Di0, the target beam size Si0, the target accelerator setting Bi0, and the range shifter insertion amount Ri0, which are the elements of the treatment plan data items F0. The setting data Fo includes an accelerator setting command Bo, a range shifter command Ro, a command current Io, a command current Ir, a beam size command So, and a target dose Do.

The irradiation control computer 22 receives irradiation records such as the measurement position coordinates Ps, the measurement dose Ds, and the measurement beam size Ss in preliminary irradiation performed without any patient and evaluates the irradiation records. The irradiation control computer 22 corrects the command current Io so as to create the command current Ir, based on the measurement position coordinates Ps, and transmits the command current Io or the command current Ir to the scanning electromagnet power source 4. The irradiation control computer 22 receives irradiation records, such as the measurement position coordinates Ps, the measurement dose Ds, and the measurement beam size Ss in main irradiation where irradiation onto a patient is actually performed, and stores the irradiation records in the main irradiation in the patient file server 56.

The irradiation control apparatus 5 outputs a trigger signal sigc, a count start signal sigh, a beam supply command Con, and a beam stop command Coff so as to control the irradiation spot and the irradiation dose at the irradiation subject 15. The irradiation control apparatus 5 changes settings of the apparatuses for each irradiation spot, in response to the a trigger signal sigc, and starts measurement of the irradiation dose at an irradiation spot, in response to the count start signal sigh; then, when the measurement dose Ds reaches the target dose Do, the irradiation control apparatus 5 performs control for the next irradiation spot. When the irradiation at all of a plurality of irradiation divisions (slices described later) obtained by dividing the irradiation subject is completed, the irradiation control apparatus 5 outputs the beam stop command Coff to the beam acceleration transport control apparatus 50 so as to stop the charged particle beam.

The scanning electromagnet power source 4 changes the setting currents for the scanning electromagnets 3a and 3b, based on the command current Io (Ir), which is outputted from the irradiation control apparatus 5 and is a control input to the scanning electromagnet 3. The beam enlargement control apparatus 17 outputs to the beam enlargement apparatus 16 the beam size command 50 for setting the beam size at the position monitor 7. The range shifter unit 23 outputs to the range shifter 21 the range shifter command Ro for changing the energy of the outgoing charged particle beam 1b.

Figure 2:
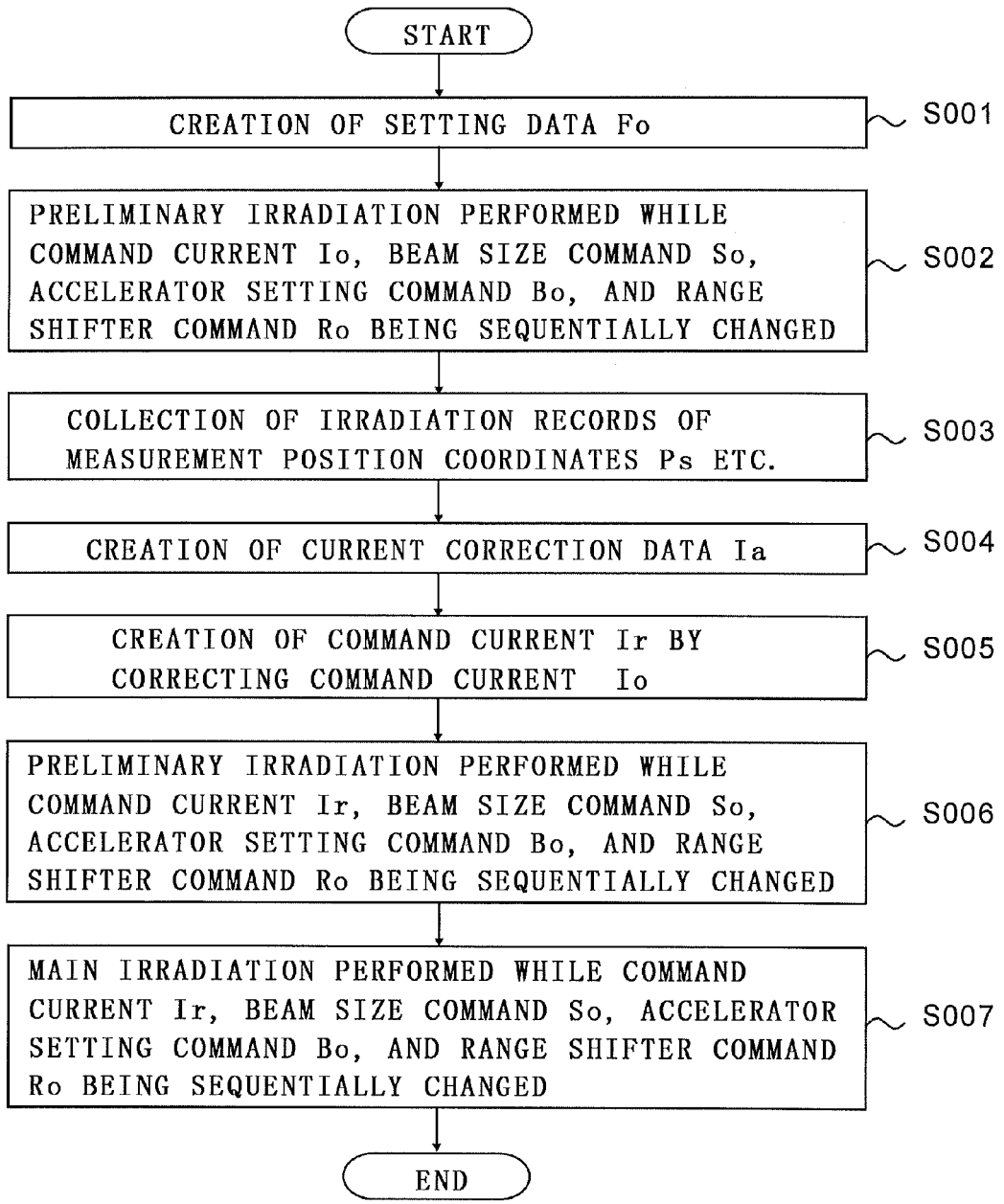
FIG. 2 is a flowchart representing an irradiation procedure according to Embodiment 1.

FIG. 2 is a flowchart representing an irradiation procedure according to Embodiment 1. The irradiation control computer 22 reads the treatment plan data items F0 in the patient file server 56 and then creates the setting data Fo. The setting data Fo are outputted to the beam acceleration transport control apparatus 50, the scanning electromagnet power source 4, the beam enlargement control apparatus 17, the range shifter unit 23, the position monitor unit 8, and the dose monitor unit and then stored at the respective memories of these apparatuses. The beam acceleration transport control apparatus stores the accelerator setting command Bo. The scanning electromagnet power source 4 stores the command current Io. The beam enlargement control apparatus 17 stores the beam size command So. The range shifter unit 23 stores the range shifter command Ro. The position monitor unit 8 stores the target irradiation position coordinates Pi and the target beam size Si. The dose monitor unit 12 stores the target dose Do (the step S001).

The irradiation control apparatus 5 outputs the trigger signal sigc for each spot and sequentially changes the command current Io, the beam size command So, the accelerator setting command Bo, and the range shifter command Ro based on the setting data Fo so as to perform preliminary irradiation (the step S002). The irradiation control computer 22 collects irradiation records such as the measurement position coordinates Ps, the measurement dose Ds, and the measurement beam size Ss in the preliminary irradiation (the step S003).

The irradiation control computer 22 creates current correction data Ia for correcting the command current Io, based on the measurement position coordinates Ps (the step S004). Based on the current correction data Ia, the irradiation control computer 22 corrects the command current Io so as to create the corrected command current Ir. The command current Ir is outputted to the scanning electromagnet power source 4 and then stored in a memory in an overwriting manner (the step S005). The irradiation control apparatus 5 outputs the trigger signal sigc and sequentially changes the corrected command current Ir, the beam size command So, the accelerator setting command Bo, and the range shifter command Ro so as to perform preliminary irradiation; then, the irradiation control apparatus 5 confirms the correction (the step S006). In the case where there exists no problem in the result of the correction, the irradiation control apparatus 5 outputs the trigger signal sigc and sequentially changes the corrected command current Ir, the beam size command So, the accelerator setting command Bo, and the range shifter command Ro so as to perform main irradiation (the step S007).

Figure 3:
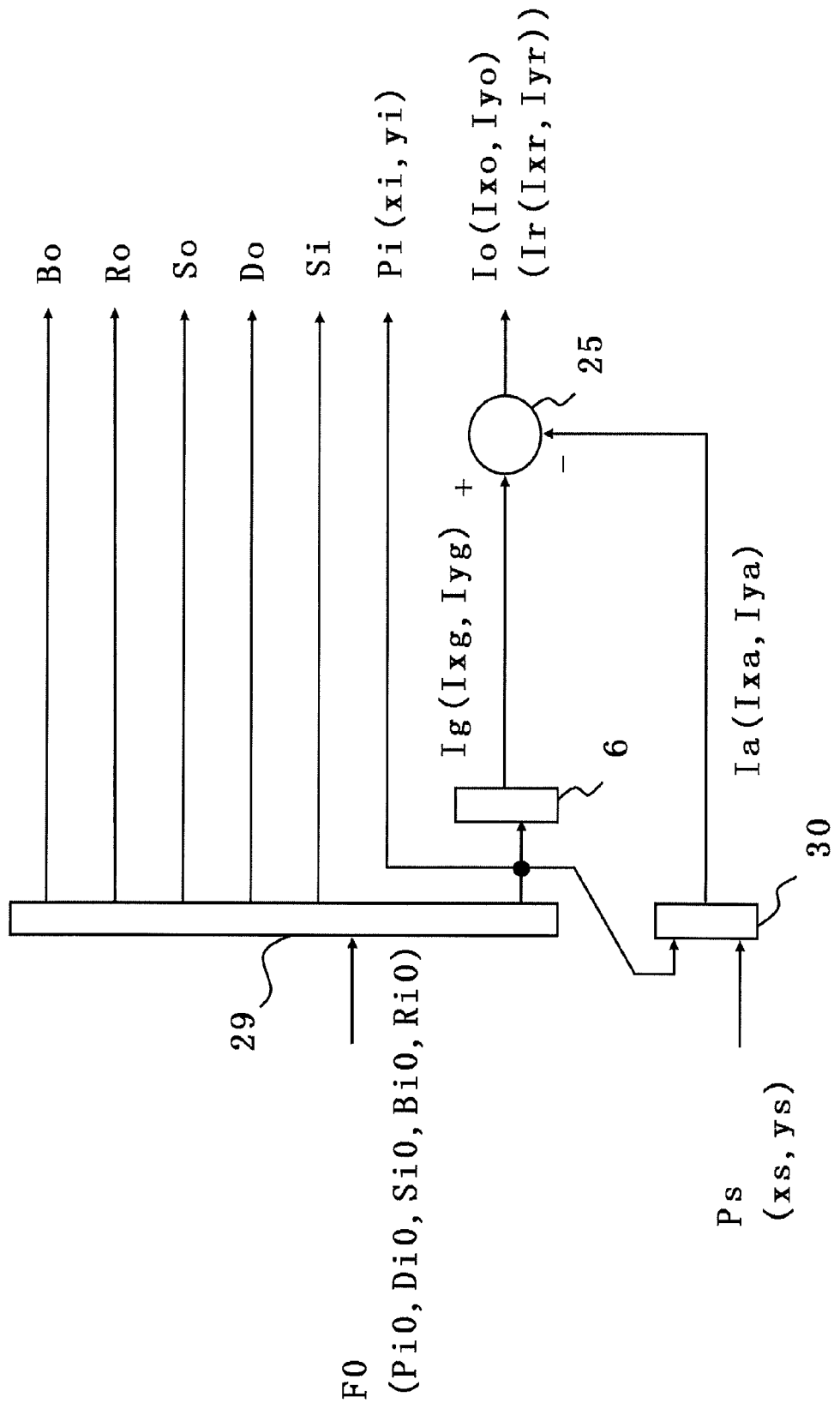
FIG. 3 is a schematic block diagram of an irradiation control computer in FIG. 1.
Figure 4:
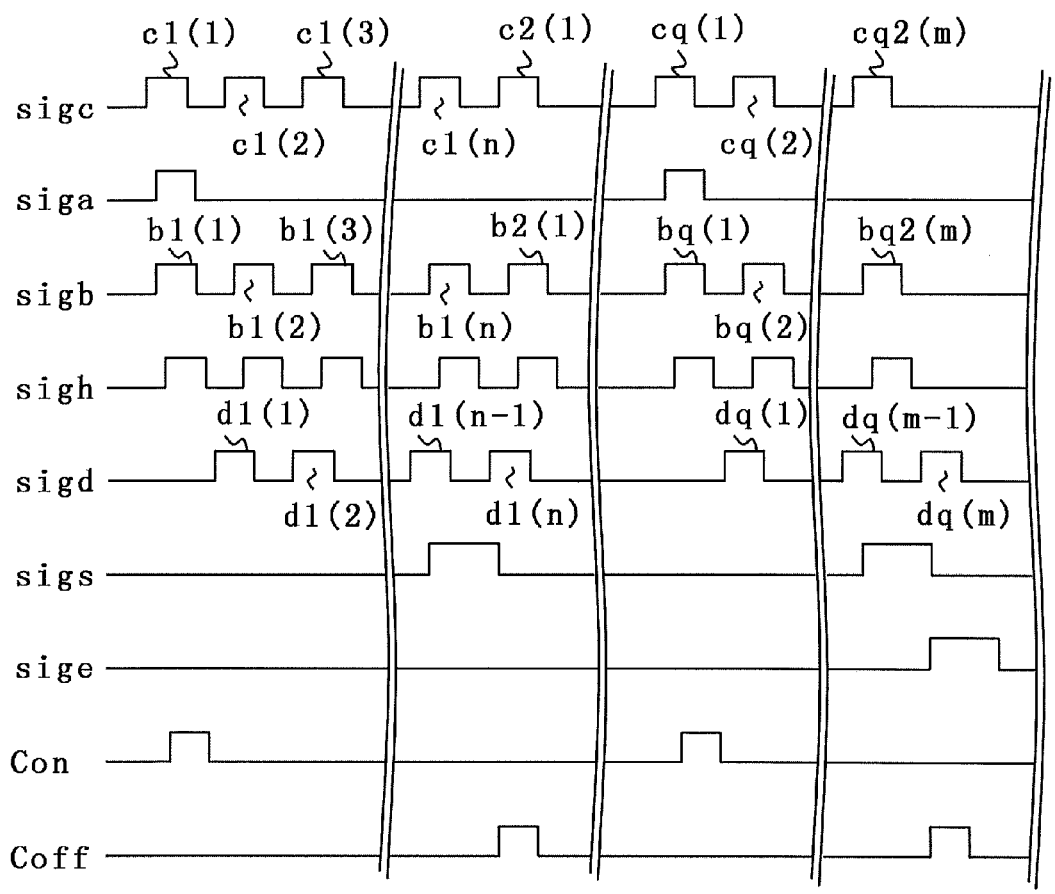
FIG. 4 is a timing chart of signal generation in an irradiation control apparatus in FIG. 1.

FIG. 3 is a schematic block diagram of a setting data creation unit, in the irradiation control computer 22, that creates the setting data Fo. The irradiation control computer 22 includes a setting data creator 29, a scanning electromagnet command value creator 6, a command value creator 25, and a correction data creator 30. FIG. 4 is a timing chart of signal generation in the irradiation control apparatus 5.

The operation of the irradiation control computer 22 and the irradiation control apparatus 5 will be explained. Here, explanation will be made based on a method in which an irradiation spot is divided in the direction of a slice, which is one of layers stacked in the Z direction, and in the X and Y directions in each slice; the charged particle beam 1 is stopped when the slice is changed, and irradiation of the charged particle beam 1 is continued when irradiation onto a single and the same slice is performed. At first, the operation of preliminary irradiation will be explained. As a preparation before irradiation, the scanning electromagnet 3 is energized until its flux density becomes the saturated magnetic flux density. The setting data creator 29 reads the treatment plan data items F0 in the patient file server 56. The correction data creator 30 outputs the current correction data Ia for preliminary irradiation to the command value creator 25 (the step S101). Because, in the case of preliminary irradiation, the command current Io is not corrected, the current correction data Ia for the preliminary irradiation is "0". The setting data creator 29 outputs to the scanning electromagnet command value creator 6 the target irradiation position coordinates Pi (xi, yi) that are rearranged in order of irradiation of an irradiation spot, which is a divided irradiation unit. The setting data creator 29 outputs the accelerator setting command Bo, the range shifter command Ro, the beam size command So, the target dose Do, the target irradiation position coordinates Pi, and the target beam size Si that are rearranged in order of irradiation of an irradiation spot, which is a divided irradiation unit, to the beam acceleration transport control apparatus 50, the range shifter unit 23, the beam enlargement control apparatus 17, the dose monitor unit 12, and the position monitor unit 8 (the step S102).

The scanning electromagnet command value generator 6 generates a basic command current Ig (Ixg, Iyg) from the target irradiation position coordinates Pi (xi, yi) (the step S103). The command value creator 25 outputs the basic command current Ig, as the command current Io (Ixo, Iyo), to the scanning electromagnet power source 4 (the step S104). The irradiation control apparatus 5 outputs the trigger signal sigc to the beam acceleration transport control apparatus 50, the scanning electromagnet power source 4, the beam enlargement control apparatus 17, the range shifter unit 23, the dose monitor unit 12, and the position monitor unit 8, so that there is started the setting for an irradiation spot onto which irradiation is performed at first (the step S105). In this situation, an irradiation spot is divided in the direction of a slice, which is one of layers stacked in the Z direction, and in the X and Y directions in each slice; therefore, each irradiation spot will be designated by a slice number and a division number in each slice. As represented in FIG. 4, there is outputted Pulse c1(1) of the trigger signal sigc for the first irradiation spot in Slice 1 (the first slice). After completing the setting of the accelerator setting command Bo, the beam acceleration transport control apparatus 50 outputs the pulse of a completion signal siga to the irradiation control apparatus 5. After having been set, the scanning electromagnet power source 4, the beam enlargement control apparatus 17, the range shifter unit 23, the dose monitor unit 12, and the position monitor unit 8 each output the pulse of an apparatus completion signal sigb to the irradiation control apparatus 5. In FIG. 4, in order to avoid complexity, only one apparatus completion signal sigb is represented; in FIG. 1, the apparatus completion signal sigb is omitted.

In response to the pulse of the completion signal siga and the pulse b1(1) of the apparatus completion signal sigb, the irradiation control apparatus 5 outputs the pulse of the count start signal sigh for instructing the start of dose measurement to the dose monitor unit 12 and the position monitor unit 8, and outputs the pulse of the beam supply command Con for instructing the generation of a beam to the beam acceleration transport control apparatus 50. The beam acceleration transport control apparatus 50 controls the beam generation apparatus 51, the accelerator 52, and the beam transport apparatus 53 so as to start irradiation of a charged particle beam (the step S106).

In response to the pulse of the count start signal sigh, the position monitor unit 8 compares the present measurement position coordinates Ps and the present measurement beam size Ss with the target irradiation position coordinates Pi and the target beam size Si, respectively, and stores the measurement position coordinates Ps and the measurement beam size Ss in a memory. When the measurement position coordinates Ps and the measurement beam size Ss exceed allowable values, an interlock is operated so as to stop the irradiation. The dose monitor unit 12 compares the target dose Do with the measurement dose Ds of the outgoing charged particle beam 1b measured by the dose monitor 11; when the measurement dose Ds exceeds the target dose Do, the dose monitor unit 12 outputs Pulse d1(1) of a dose completion signal sigd to the irradiation control apparatus 5 and the position monitor unit 8. The dose monitor 11 stores in a memory the measurement dose Ds at a time when the pulse of the dose completion signal sigd is outputted (the step S107).

Next, there is started setting for an irradiation spot that is irradiated secondly (the step S108). There is outputted Pulse c1(2) of the trigger signal sigc for the second irradiation spot in Slice 1. Because of the irradiation spot in a single and the same slice, the accelerator setting command Bo and the range shifter command Ro are not changed. After having been set, the scanning electromagnet power source 4, the beam enlargement control apparatus 17, the dose monitor unit 12, and the position monitor unit 8 each output Pulse b1(2) of the apparatus completion signal sigb to the irradiation control apparatus 5.

In response to Pulse b1(2) of the apparatus completion signal sigb, the irradiation control apparatus 5 outputs the pulse of the count start signal sigh for instructing the start of dose measurement to the dose monitor unit 12 and the position monitor unit 8. The dose monitor unit 12 measures the irradiation dose of the second irradiation spot (the step S109). In addition, the dose monitor unit 12 has a spot counter for measuring the irradiation dose at each irradiation spot and an inter-spot counter for measuring the irradiation dose of a charged particle beam traveling from a spot to another spot. The measurement dose in the time from a time instant when the pulse of the dose completion signal sigd is outputted to a time instant when the count start signal sigh is received corresponds to the irradiation dose (inter-spot irradiation dose) at a time when the charged particle beam 1 travels to the next spot. In response to the pulse of the count start signal sigh, the inter-spot irradiation dose is stored in a memory.

In response to the pulse of the count start signal sigh, the position monitor unit 8 compares the present measurement position coordinates Ps and the present measurement beam size Ss with the target irradiation position coordinates Pi and the target beam size Si, respectively, and stores the measurement position coordinates Ps and the measurement beam size Ss in a memory. When the measurement position coordinates Ps and the measurement beam size Ss exceed allowable values, an interlock is operated so as to stop the irradiation. The dose monitor unit 12 compares the target dose Do with the measurement dose Ds of the outgoing charged particle beam 1b measured by the dose monitor 11; when the measurement dose Ds exceeds the target dose Do, the dose monitor unit 12 outputs Pulse d1(2) of a dose completion signal sigd to the irradiation control apparatus 5 and the position monitor unit 8. The dose monitor 11 stores in a memory the measurement dose Ds at a time when the pulse of the dose completion signal sigd is outputted (the step S110).

The order of irradiation is changed in turn; the process from the step S108 to the step S110 is repeated until irradiation is performed onto the last irradiation spot (number: n) in a slice (the step S111). In the last irradiation spot in a slice, in response to Pulse c1(n) of the trigger signal sigc, the dose monitor 11 outputs the pulse of a slice last signal sigs to the irradiation control apparatus 5. The dose monitor 11 can detect that setting for the last irradiation spot in a slice has been made, based on information on the number of spots for each slice number.

In response to the pulse of the slice last signal sigs and Pulse d1(n) of the dose completion signal sigd, the irradiation control apparatus 5 outputs to the beam acceleration transport control apparatus 50 the beam stop command Coff for instructing the stoppage of a beam. There is outputted Pulse c2(1) of the trigger signal sigc for the first irradiation spot in Slice 2 (the step S112).

The process from the step S006 to the step S112 is repeated so that irradiation onto each slice is performed (the step S113). In the last irradiation spot (number: m) in the last slice (number: q), when outputting Pulse dq(m) of the dose completion signal sigd, the dose monitor 11 outputs the pulse of an irradiation end signal sige to the irradiation control computer 22. In the last irradiation spot in the last slice (number: q), the pulse of the trigger signal sigc is not outputted.

In response to the pulse of the irradiation end signal sige, the irradiation control computer 22 collects the measurement dose Ds from the dose monitor unit 12. The irradiation control computer 22 collects the measurement position coordinates Ps (xs, ys) of the outgoing charged particle beam 1*b* and the measurement beam size Ss from the position monitor unit 8 (the step S114).

Next, there will be explained the operation of the preliminary irradiation utilizing the corrected command current Ir and the operation of the main irradiation. In addition, the operation of the preliminary irradiation utilizing the corrected command current Ir and the operation of the main irradiation are similar to each other; therefore, the main irradiation will be explained. As a preparation before irradiation, the scanning electromagnet 3 is energized until its flux density becomes the saturated magnetic flux density. The setting data creator 29 reads the treatment plan data items F0 in the patient file server 56. In the case where the treatment plan data items F0 are stored in the irradiation control computer 22, the stored data may be utilized. The correction data creator 30 creates the current correction data Ia for the main irradiation (the step S115). There will be described later the method of creating the current correction data Ia for correcting the command current Io. The setting data creator 29 outputs to the scanning electromagnet command value creator 6 the target irradiation position coordinates Pi (xi, yi) that are rearranged in order of irradiation of an irradiation spot, which is a divided irradiation unit. The setting data creator 29 outputs the accelerator setting command Bo, the range shifter command Ro, the beam size command So, the target dose Do, the target irradiation position coordinates Pi, and the target beam size Si that are rearranged in order of irradiation of an irradiation spot, which is a divided irradiation unit, to the beam acceleration transport control apparatus 50, the range shifter unit 23, the beam enlargement control apparatus 17, the dose monitor unit 12, and the position monitor unit 8 (the step S116).

The scanning electromagnet command value generator 6 generates a basic command current Ig (Ixg, Iyg) from the target irradiation position coordinates Pi (xi, yi) (the step S117). The command value creator 25 outputs a command current (Ig−Ia) obtained by correcting the basic command currents Ig with the current correction data Ia, as the command current Ir (Ixr, Iyr), to the scanning electromagnet power source 4 (the step S118). The operation hereinafter is similar to the process from the step S105 to the step S114, when the command current Io is read as the command current Ir.

Figure 5:
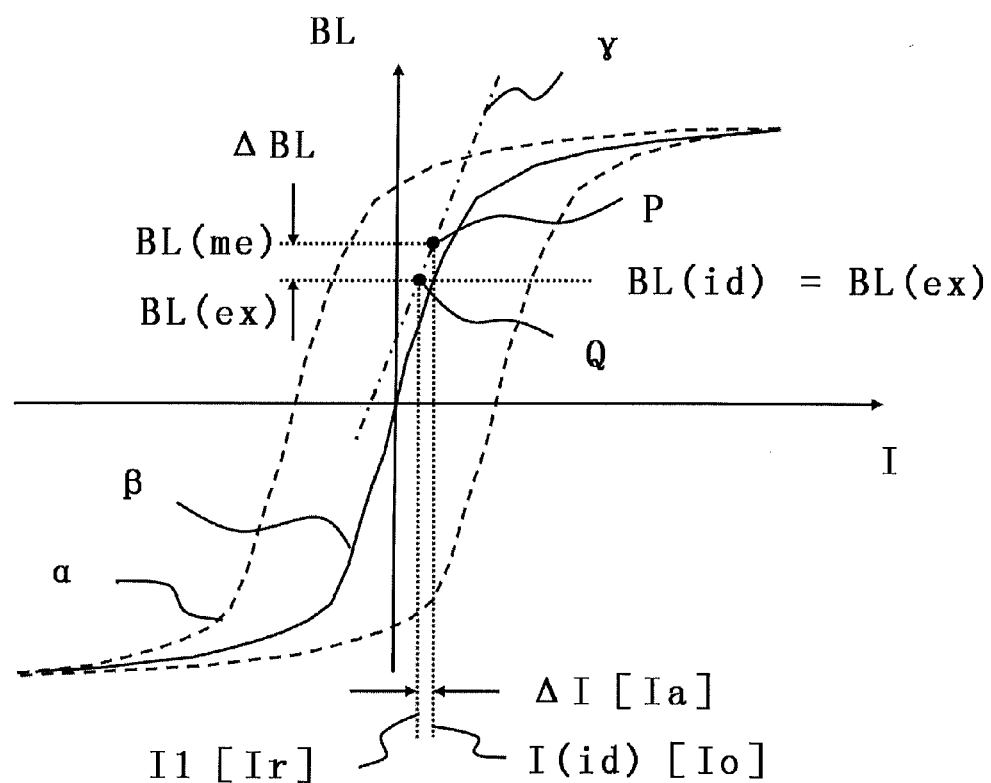
FIG. 5 is a graph for explaining a method of correcting a command current.

The method of creating the current correction data Ia will be explained. FIG. 5 is a graph for explaining a method of correcting a command current. There is measured the BL product vs. the current I, which is outputted to the scanning electromagnet 3 due to the command current Io applied to the scanning electromagnet power source 4. The BL product is multiplication product of the intensity B of the magnetic field and the effective length L of the magnetic pole of the scanning electromagnet 3. There is drawn a maximum hysteresis curve a that passed through the saturated magnetic flux density. By averaging the one portion of the maximum hysteresis curve α, which is drawn in such a way that the current increase, and the other portion of the maximum hysteresis curve α, which is drawn in such a way that the current decreases, the center line β of the hysteresis loop is obtained.

The current value I(id) set through the command current Io is determined by the target irradiation position coordinates Pi, at which irradiation is performed, the center line β of the hysteresis loop, the energy of the outgoing charged particle beam 1*b*, and the distance between the position at which the scanning electromagnet 3 is disposed and the irradiation position. While considering the Lorentz force (Fleming's left-hand rule) exerted on the charged particle beam 1, the value of the BL product can be obtained from the position coordinates of the charged particle beam 1. The command current Io is a command value that corresponds to the current I(id) at the intersection point P' (not represented) of the value BL(id) of the ideal BL product calculated from the target irradiation position coordinates Pi with the center line β of the hysteresis loop. BL(id) is the expected value BL(ex) of the value of the BL product to be measured.

A value BL(me) of the BL product is calculated from the measured measurement position coordinates Ps. The point P in FIG. 5 is the actually measured value. There will be considered a case where the value BL(me) of the measured BL product is displaced by ΔBL from the expected value BL(ex). In order to correct the current, the displacement by ΔBL is made by use of a straight line having a gradient K, which is a tangential line at the intersection point P' at which the command current Io is obtained. In order to make a correction, there is obtained the current value I1 at which the BL product becomes BL(ex). After the current value I1 is obtained, there can be generated the command current Ir for setting the current value to the current value I1 corresponding to BL(id). In such a way as described above, the displacement of the charged particle beam 1 due to the hysteresis of the scanning electromagnet can be made to fall within a tolerance range.

The straight line (dashed line) y is a line having the gradient K that is the same as the gradient of the tangential line, at the current value I(id), of the center line β. The gradient K can be expressed by the equation (1), and the corrected current value I1 can be expressed by the equation (2).

$$K = \frac{dBL}{dI}(id) \qquad (1)$$

$$I1 = I(id) - \Delta BL / K \qquad (2)$$

where ΔBL=BL(me)−BL(ex).

The correction current value ΔI to be set through the current correction data Ia is ΔBL/K.

In the particle beam therapy system according to Embodiment 1, the preliminary irradiation is performed with an excitation pattern the same as the excitation pattern, according to the setting data Fo base on the treatment plan data items F0, of the scanning electromagnet in the main-irradiation plan, i.e., the preliminary irradiation is performed in such a way that the order, for controlling the irradiation dose, of irradiation onto the irradiation spots is the same as the order of the main irradiation; therefore, there can be obtained the measurement position coordinates Ps of the charged particle beam 1*b* on which the effect of the hysteresis of the scanning electromagnet 3 is reflected. Because the command current Io is corrected based on the setting data Fo and the current correction data Ia created on the basis of the measurement position coordinates Ps of the charged particle beam 1*b* on which the effect of the hysteresis of the scanning electromagnet 3 is reflected, the displacement of the charged particle beam 1*b* due to the hysteresis of the scanning electromagnet 3 can be corrected. As a result, the effect of the hysteresis of the scanning electromagnet 3 is reduced, so that high-accuracy beam irradiation can be realized.

In the particle beam therapy system according to Embodiment 1, as the preparation before the irradiation, the scanning electromagnet 3 is excited up to the saturated magnetic flux density; therefore, the effect of the hysteresis of the scanning electromagnet 3 on the first irradiation spot for the charged particle beam 1 can be made almost constant. Thus, in all of the irradiation spots onto which irradiation is performed, the effect of the hysteresis of the scanning electromagnet 3 on the preliminary irradiation, which is performed with the same excitation pattern as the excitation pattern of the scanning electromagnet in the main irradiation plan, can be made almost constant. Therefore, even in the case where the main irradiation is performed two or more times with a single and the same excitation pattern, high-accuracy beam irradiation can be realized without making a correction through the preliminary irradiation each time the main irradiation is performed.

In the particle beam therapy system according to Embodiment 1, the depth-direction (Z direction) position coordinates of the irradiation subject 15 is controlled by varying the energy of the incident charged particle beam 1a through change in the acceleration energy of the accelerator 52 and by varying the energy of the outgoing charged particle beam 1b through the range shifter 21; therefore, because the change in the acceleration energy of the accelerator 52 can be minimized, the irradiation time can be shortened, whereby the time of process prior to the main irradiation can be shortened.

As described above, in the particle beam therapy system according to Embodiment 1, there are provided the irradiation management apparatus 32 that controls the scanning electromagnet 3, based on the target irradiation position coordinates Pi of the charged particle beam 1b, and the position monitor 7 that measures the measurement position coordinates Ps of the charged particle beam 1b, and the irradiation management apparatus 32 has the command value creator 25 that outputs the control input Io (Ir) to the scanning electromagnet 3, based on the target irradiation position coordinates Pi and the correction data Ia created on the basis of the measurement position coordinates Ps, measured by the position monitor 7 in the preliminary irradiation in which the excitation pattern of the scanning electromagnet is the same as that of the main irradiation plan, and the target irradiation position coordinates Pi; thus, the effect of the hysteresis of the scanning electromagnet 3 is reduced, so that high-accuracy beam irradiation can be realized.

It may be allowed that, after the step S006 in FIG. 2 in which the correction is confirmed, the current correction data Ia is stored in the memory of the irradiation control computer or the patient file server 56 and then the stored current correction data Ia is read and supplied to the command value creator 25. In such a way as described above, interruption and resumption can be performed before the main irradiation; thus, the particle beam therapy system can efficiently be operated.

Embodiment 2

Figure 6A:
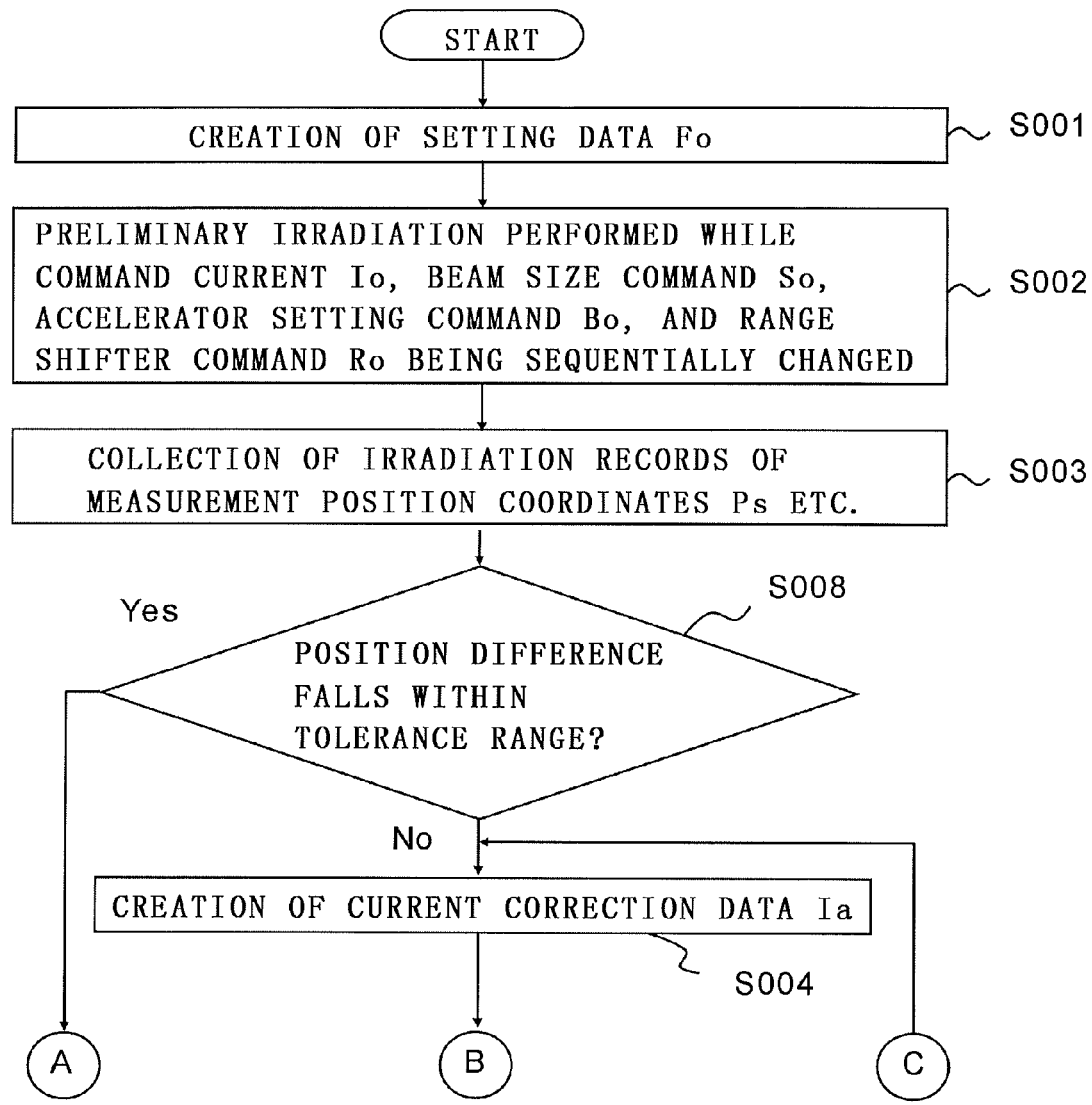
FIG. 6 is a flowchart representing an irradiation procedure according to Embodiment 2 of the present invention.
Figure 6B:
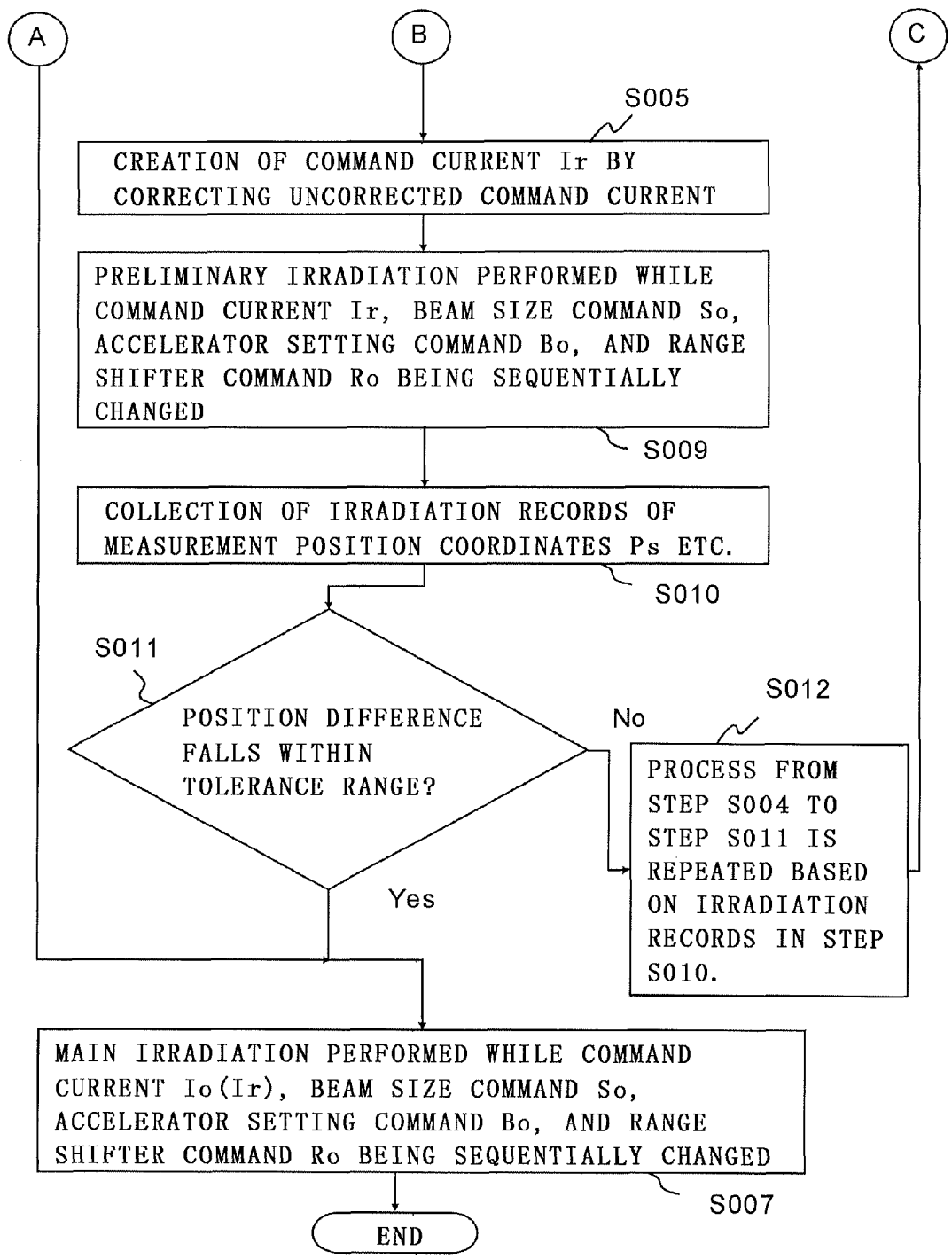

FIG. 6 is a flowchart representing an irradiation procedure according to Embodiment 2 of the present invention. Embodiment 2 is different from Embodiment 1 in that, in the confirmation of the preliminary irradiation based on the command current Io, the irradiation position difference is evaluated, and the correction based on the current correction data Ia is repeated until the irradiation position difference falls within a tolerance range.

In FIG. 6, the steps from S001 to S007 are similar to those in Embodiment 1, and the steps S008 to S012 are added. In the step S008, based on the irradiation record collected in the step S003, it is determined whether or not the position difference between the measurement position coordinates Ps and the target irradiation position coordinates Pi is within the tolerance range. In the case where the position difference between the measurement position coordinates Ps and the target irradiation position coordinates Pi is within the tolerance range, the step S008 is followed by the step S007, and then the main irradiation is carried out without performing any correction.

In the case where the position difference between the measurement position coordinates Ps and the target irradiation position coordinates Pi is not within the tolerance range, the step S008 is followed by the step S004, the current correction data Ia for correcting the command current Io is created based on the measurement position coordinates Ps. In the step S005, the corrected command current Ir is created; in the step S009, the corrected command current Ir, the beam size command So, the accelerator setting command Bo, and the range shifter command Ro are sequentially changed; then, the preliminary irradiation is performed. In the step S010, the irradiation control computer 22 collects irradiation records such as the measurement position coordinates Ps, the measurement dose Ds, and the measurement beam size Ss in the preliminary irradiation. In the step S011, based on the irradiation records collected in the step S010, it is determined whether or not the position difference between the measurement position coordinates Ps and the target irradiation position coordinates Pi is within the tolerance range. In the case where the position difference between the measurement position coordinates Ps and the target irradiation position coordinates Pi is within the tolerance range, the step S011 is followed by the step S007, and then the main irradiation is carried out without performing correction again.

In the case where the position difference is not within the tolerance range, the step S011 is followed by the step S012, and then the process from the step S004 to the step S011 is repeated based on the irradiation records collected in the step S010.

A determination device 40 for performing determination in each of the steps S008 and S011 is realized with a CPU 41 and a memory 42 of the irradiation control computer 22.

In the particle beam therapy system according to Embodiment 2, the position difference in the preliminary irradiation based on the command current Io is evaluated, and the correction based on the current correction data Ia is repeated until the position difference falls within a predetermined range; therefore, the displacement of the charged particle beam 1b due to the hysteresis of the scanning electromagnet 3 can be corrected more accurately than in Embodiment 1. As a result, the effect of the hysteresis of the scanning electromagnet 3 is reduced, so that further high-accuracy beam irradiation can be realized. In the case where, in the preliminary irradiation based on the command current Io, the position difference falls within the tolerance range, no correction is performed; thus, there can be shortened the time for determining the setting data Fo to be applied to the main irradiation.

In addition, in Embodiment 1, an example where the preliminary irradiation is performed again prior to the main irradiation has been explained; however, it may be allowed that, as the confirmation irradiation of a particle beam therapy system, the confirmation irradiation based on the current correction data Ia is performed, while omitting the procedure in the step S006.

Additionally, explanation has been made with an irradiation method in which the charged particle beam 1 is stopped when slices are changed, and the charged particle beam 1 is continuously irradiated when irradiation is performed within a single and the same slice; however, the present invention can be applied to other irradiation methods such as the spot-scanning method in which the charged particle beam 1 is stopped for each irradiation spot and the raster-scanning method. Additionally, in the raster-scanning method, even though there exists no irradiation spot as a discrete position for which a beam is stopped, a position in the irradiation subject 15, for which the irradiation dose is controlled, may be referred to as an irradiation spot for controlling the irradiation dose. In addition, in the raster-scanning method, the folding point of the charged particle beam 1 or the like is a changing point of the increase/decrease pattern of the current of the scanning electromagnet 3; it may be allowed that the current correction data Ia is created based on the measurement position coordinates and the target irradiation position coordinates corresponding to the changing point of the increase/decrease pattern of the current of the scanning electromagnet 3.

INDUSTRIAL APPLICABILITY

A particle beam therapy system according to the present invention can preferably be applied to a particle beam therapy system utilized in the medical field and R&Ds.

DESCRIPTION OF REFERENCE NUMERALS

| | |
|---|---|
| 1: | charged particle beam |
| 1a: | incident charged particle beam |
| 1b: | outgoing charged particle beam |
| 3: | scanning electromagnet |
| 3a: | X-direction scanning electromagnet |
| 3b: | Y-direction scanning electromagnet |
| 6: | scanning electromagnet command value creator |
| 7: | position monitor |
| 15: | irradiation subject |
| 25: | command value creator |
| 30: | correction data creator |
| 32: | irradiation management apparatus |
| 40: | determination device |
| 52: | accelerator |
| Io: | command current |
| Ir: | command current |
| Ig: | command current |
| Ia: | current correction data |
| Pi: | target irradiation position coordinates |
| Ps: | measurement position coordinates |

The invention claimed is:

1. A particle beam therapy system that irradiates a charged particle beam, accelerated by an accelerator and scanned by a scanning electromagnet, onto an irradiation subject, the particle beam therapy system comprising:
an irradiation management apparatus that controls the scanning electromagnet, based on target irradiation position coordinates of the charged particle beam; and
a position monitor that measures measurement position coordinates of the charged particle beam, wherein the irradiation management apparatus has a command value creator that outputs a control input to the scanning electromagnet, for scanning the charged particle beam, based on the target irradiation position coordinates and correction data, said correction data having been created in a preliminary irradiation,
wherein (i) said preliminary irradiation is performed prior to said irradiation of said subject and (ii) an excitation pattern of the scanning electromagnet of said preliminary irradiation is the same as an excitation pattern of the scanning electromagnet of a main irradiation plan for actual irradiation of the subject, and
wherein the correction data is created on a basis of the target irradiation position coordinates and the measurement position coordinates measured by the position monitor in said preliminary irradiation.

2. The particle beam therapy system according to claim 1, wherein, the irradiation management apparatus includes (i) a correction data creator that creates the correction data in said preliminary irradiation and (ii) a scanning electromagnet command value creator that creates a basic control input from the measurement position coordinates, wherein
the command value creator outputs, as the control input, a corrected control input obtained by correcting the basic control input, created by the scanning electromagnet command value creator, with the correction data created by the correction data creator.

3. The particle beam therapy system according to claim 2, wherein the correction data is created based on a value obtained by dividing by a coefficient K the difference $\Delta BL$ between the value $BL(me)$ of a BL product of the scanning electromagnet calculated from the measurement position coordinates measured in the preliminary irradiation and the value $BL(ex)$ of a BL product of the scanning electromagnet calculated from the target irradiation position coordinates; and
the coefficient K is a gradient of a tangential line at a point, at which the value of the BL product is $BL(ex)$, on the center line of the hysteresis loop configured with the BL product and the current of the scanning electromagnet.

4. The particle beam therapy system according to claim 3, wherein the irradiation management apparatus has a determination device that determines whether or not the position difference between the measurement position coordinates and the target irradiation position coordinates falls within a predetermined tolerance range; in the case where the position difference does not fall within the predetermined range, the irradiation management apparatus creates the correction data; and in the case where the position difference falls within the predetermined range, the irradiation management apparatus sets the control input to the scanning electromagnet to a value the same as a value in the preliminary irradiation.

5. The particle beam therapy system according to claim 2, wherein the irradiation management apparatus has a determination device that determines whether or not the position difference between the measurement position coordinates and the target irradiation position coordinates falls within a predetermined tolerance range; in the case where the position difference does not fall within the predetermined range, the irradiation management apparatus creates the correction data; and in the case where the position difference falls within the predetermined range, the irradiation management apparatus sets the control input to the scanning electromagnet to a value the same as a value in the preliminary irradiation.

6. The particle beam therapy system according to claim 1, wherein the correction data is created based on a value obtained by dividing by a coefficient K the difference $\Delta BL$ between the value $BL(me)$ of a BL product of the scanning electromagnet calculated from the measurement position coordinates measured in the preliminary irradiation and the value $BL(ex)$ of a BL product of the scanning electromagnet calculated from the target irradiation position coordinates; and
the coefficient K is a gradient of a tangential line at a point, at which the value of the BL product is $BL(ex)$, on the center line of the hysteresis loop configured with the BL product and the current of the scanning electromagnet.

7. The particle beam therapy system according to claim 6, wherein the irradiation management apparatus has a determination device that determines whether or not the position difference between the measurement position coordinates and the target irradiation position coordinates falls within a predetermined tolerance range; in the case where the position difference does not fall within the predetermined range, the irradiation management apparatus creates the correction data; and in the case where the position difference falls within the predetermined range, the irradiation management apparatus sets the control input to the scanning electromagnet to a value the same as a value in the preliminary irradiation.

8. The particle beam therapy system according to claim 1, wherein the irradiation management apparatus has a determination device that determines whether or not the position difference between the measurement position coordinates and the target irradiation position coordinates falls within a predetermined tolerance range; in the case where the position difference does not fall within the predetermined range, the irradiation management apparatus creates the correction data; and in the case where the position difference falls within the predetermined range, the irradiation management apparatus sets the control input to the scanning electromagnet to a value the same as a value in the preliminary irradiation.

9. An irradiation method for irradiating a charged particle beam onto an irradiation subject, the method comprising:

creating irradiation setting data, said setting data including at least target irradiation position coordinates and dosage amounts;

outputting a control input to a scanning electromagnet performing a preliminary irradiation according to said setting data, wherein (i) said preliminary irradiation is performed prior to performing an actual irradiation on a subject and (ii) a scanning-electromagnet excitation pattern of the preliminary irradiation is the same as a scanning-electromagnet excitation pattern of actual irradiation;

recording, in said preliminary irradiation, measurement data including at least measurement position coordinates;

creating correction data based on the target irradiation position coordinates and the measurement position coordinates measured in said preliminary irradiation; and correcting the control input to the scanning electromagnet based on the correction data created in preliminary irradiation to create a corrected control input for actual irradiation on a subject.

* * * * *